United States Patent

Barton et al.

[11] Patent Number: 5,283,271
[45] Date of Patent: Feb. 1, 1994

[54] 3,5-DIPHENYL OR SUBSTITUTED 3,5-DIPHENYL-1-HYDROXY-1,2-DIHYDROIMIDAZOLE-2-THIONES

[75] Inventors: Derek H. R. Barton, College Station; Catherine Tachdjian, Bryan, both of Tex.

[73] Assignee: Olin Corporation, Cheshire, Conn.

[21] Appl. No.: 997,051

[22] Filed: Dec. 28, 1992

[51] Int. Cl.$^5$ .............. C08K 5/36; A61K 31/415; A61K 7/40; C11D 9/50; C07D 233/42; C09K 15/30
[52] U.S. Cl. .................. 523/122; 106/18.22; 252/106; 252/107; 524/106; 514/398; 548/316.4; 548/316.7
[58] Field of Search .......... 523/122; 548/316.7, 548/316.4; 106/18.22; 252/106, 107; 514/398; 524/106

[56] References Cited

U.S. PATENT DOCUMENTS

| | | | |
|---|---|---|---|
| 3,369,027 | 2/1968 | Klauke et al. | 523/122 |
| 3,448,116 | 6/1969 | McCaully et al. | 548/316.7 |
| 3,723,435 | 3/1973 | Furia | 523/122 |
| 3,732,244 | 5/1973 | Boocock et al. | 548/316.7 |
| 3,892,699 | 7/1975 | Weisse | 523/122 |
| 3,905,996 | 9/1975 | Perronnet et al. | 548/316.7 |
| 4,401,770 | 8/1983 | Hance | 521/120 |
| 4,818,436 | 4/1989 | French et al. | 252/400.23 |
| 4,935,061 | 6/1990 | French et al. | 106/170 |
| 5,104,993 | 4/1992 | Arduengo | 548/316.4 |

*Primary Examiner*—Veronica P. Hoke
*Attorney, Agent, or Firm*—Dale L. Carlson

[57] ABSTRACT

A compound selected from the group consisting of 3,5-diphenyl- and substituted 3,5-diphenyl-1-hydroxy-1,2-dihydroimidazole-2-thiones, and combinations thereof. Also disclosed is a process for producing the compound and an antimicrobial composition comprising the compound and at least one component selected from the group consisting of soaps, shampoos, skin care medicaments, cosmetics and paints.

11 Claims, No Drawings

3,5-DIPHENYL OR SUBSTITUTED 3,5-DIPHENYL-1-HYDROXY-1,2-DIHYDROIMIDAZOLE-2-THIONES

FIELD OF THE INVENTION

This invention relates to novel 3,5-diphenyl or substituted 3,5-diphenyl-1-hydroxy-1,2-dihydroimidazole-2-thiones and their use as biocides. These compounds exhibit good biocidal activity, Particularly antifungal activity.

BACKGROUND OF THE INVENTION

Compounds exhibiting biocidal activity are well known in the art. For example, pyrithione salts, such as zinc pyrithione, are known to Provide excellent biocidal activity, including broad spectrum anti-bacterial and anti-fungal activity. There are many uses for these pyrithiones. By way of illustration, U.S. Pat. No. 4,818,436 discloses the use of pyrithiones in metal working fluids, U.S. Pat. No. 4,401,770 discloses urethane shoe inserts having antimicrobial activity; and U.S. Pat. No. 4,935,061 discloses their use in paints.

Despite the excellent biocidal (particularly fungicidal) activity attributable to pyrithione salts, these compounds do have drawbacks for certain applications, most notably limited solubility in organic solvents. Accordingly, new compounds exhibiting excellent biocidal activity, but also exhibiting good solubility in organic solvents would be useful to the biocides manufacturing community.

SUMMARY OF THE INVENTION

In one aspect, the present invention relates to a compound selected from the group consisting of 3,5-diphenyl- and substituted 3,5-diphenyl-1-hydroxy-1,2-dihydroimidazole-2-thiones, and combinations thereof.

In another aspect, this invention relates to a process for producing the above-mentioned compounds which comprises the following steps:

(a) reacting aniline or substituted aniline(s) with phenacyl halide or substituted phenacyl halide(s) in the Presence of a base in an organic solvent to form N-phenacylaniline or substituted N-phenacylaniline(s);

(b) reacting N-phenylacylaniline or substituted N-phenylacylaniline(s) with chlorothiono (or dithio) formic acid esters and a base in an organic solvent to form N-(2-oxo-2-phenylethyl)-N-phenylthiono (or dithio) carbamic acid ester(s) or substituted N-(2-oxo-2-Phenylethyl)-N-phenylthiono (or dithio) carbamic acid ester(s), (c) reacting N-(2-oxo-2-phenylethyl)-N-phenylthiono (or dithio) carbamic acid esters or substituted N-(2-oxo-2-Phenylethyl)-N-phenylthiono (or dithio) carbamic acid esters with hydroxylamine hydrochloride and a base in an organic solvent to form 3,5-diphenyl-1-hydroxy-1,2-dihydroimidazole-2-thione or substituted 3,5-diphenyl-1-hydroxy-1,2-dihydro imidazole-2-thione.

In yet another aspect, this invention relates to a composition comprising an antimicrobial effective amount of a compound selected from the group consisting of 3,5-diphenyl- and substituted 3,5-diphenyl-1-hydroxy-1,2-dihydroimidazole-2-thiones, and combinations thereof, and at least one component selected from the group consisting of soaps, shampoos, skin care medicaments, cosmetics and paints.

In still another aspect, the invention relates to a method for inhibiting the growth of microorganisms by contacting said microorganisms with an antimicrobial effective amount of the compounds of this invention.

These and other aspects will become apparent upon reading the following detailed description of the invention.

DETAILED DESCRIPTION OF THE INVENTION

The novel 3,5 diphenyl or substituted 3,5-diphenyl-1-hydroxy-1,2-dihydroimidazole-2-thione compounds of this invention are represented by the following empirical structural formula:

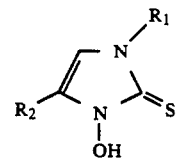

wherein $R_1$ and $R_2$ are Phenyl and/or substituted phenyl groups. The synthesis of these compounds is illustrated by the following reaction sequence:

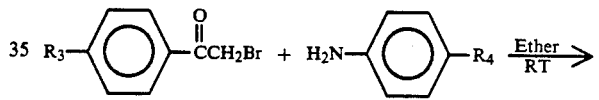

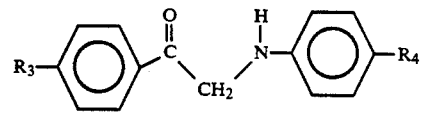

$R_3$ = H, $R_4$ = H (EX. I)
$R_3$ = H, $R_4$ = OCH$_3$ (EX. II)
$R_3$ = OCH$_3$, $R_4$ = H (EX. III)

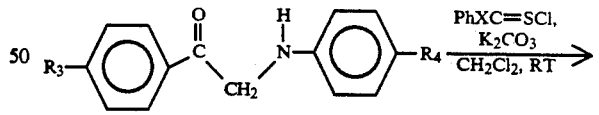

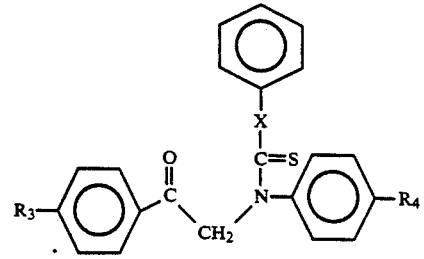

$R_3$ = H, $R_4$ = H, X = O (EX. I)
$R_3$ = H, $R_4$ = OCH$_3$, X = O (EX. II)
$R_3$ = OCH$_3$, $R_4$ = H, X = S (EX.III)

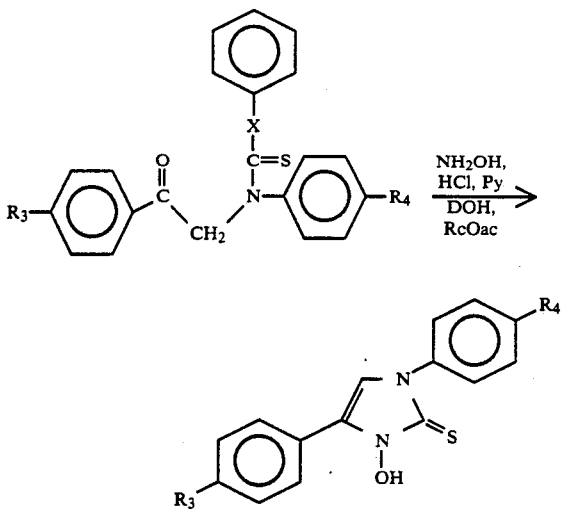

to produce the following compounds:
 compound (1) R$_3$ = H, R$_4$ = H (EX. I)
 compound (2) R$_3$ = H, R$_4$ = OCH$_3$ (EX. II)
 compound (3) R$_3$ = OCH$_3$, R$_4$ = H (EX. III)

As used in the process of the Present invention, the term "substituted" is intended to designate phenyl substitutions (i.e., substitutions on the recited phenyl ring), such as, for example, halogen (e.g., chlorine or fluorine), lower alkyl containing between one and six carbons, lower alkoxy containing between one and six carbons (such as methoxy or ethoxy), carboxylic acid, carboxylic acid ester(s), and nitro-substitutions.

The reactions of the Process of this invention are suitably conducted at atmospheric pressure, although higher or lower Pressures may be used if desired. Suitable reaction temperatures for step (a) range between a temperature of about 0° C. to about 80° C., preferably room (ambient) temperature. Suitable reaction temperatures for step (b) range between a temperature of about −40° C. to about 60° C., preferably room temperature. Suitable reaction temperatures for step (c) range between a temperature of about 60° C. to about 110° C., preferably at 80° C. Total reaction time for the Process of this invention can vary over a wide range, but is Preferably between 30 minutes and 48 hours for step (a); 5 hours to 20 hours for step (b), and 5 hours to 30 hours for step (c).

The reactions of the process of this invention are suitably carried out in the presence of a base and an organic solvent. Suitable bases include pyridine, triethylamine and other tertiary amine bases, potassium carbonate, aniline or substituted anilines, DABCO (1,4-diazabicyclo(2.2.2)octane), DBU (1,8-diazabicyclo(5.4.-0)undec-7-ene), DBN (1,5-diazabicyclo(4.3.0)non-5-ene, t-butyltetramethyl-guanidine, combinations thereof, and the like. Preferred bases for step (a) include anilines and substituted anilines. A preferred base for step (b) is potassium carbonate. A preferred base for step (c) is pyridine. Although not wishing to be bound by any particular theory, it is believed by the present inventors that the base acts as an acid scavenger for by-product acid formed in each of the reaction steps. Preferably, the base is employed in at least an amount equal to the number of moles for each reactant, and in step (c) it is preferred to employ at least 2 equivalents of base per mole of each reactant.

Suitable organic solvents include, for example, alcohol, ether, and acetone, methylene chloride, benzene, toluene, pyridine, tetrahydrofuran ("THF"), and combinations thereof. The Preferred solvent for step (a) is ether, for step (b) is methylene chloride, and for step (c) is a mixture of alcohol and THF.

The molar ratio of reactants for each of the three reaction steps of the process of this invention can vary over a wide range, but is preferably between 10:1 and 1:10, more preferably between 2:1 and 1:2, most preferably about 1:1.

The antimicrobial composition of this invention suitably comprise a compound selected from the group consisting of 3,5-phenyl or substituted 3,5-diphenyl-1-hydroxy-1,2-dihydroimidazole-2-thiones, and combinations thereof and at least one component selected from the group consisting of soaps, shampoos, skin care medicaments, cosmetics and paints. By the term "antimicrobial effective amount" is meant an amount sufficient to impart to the compositions resistance against microbial attack by fungi and/or bacteria. Preferably the antimicrobial compounds are employed in the composition in an amount of between about 0.01 and about 10 weight percent, more preferably between about 0.01 and about 5 percent, based upon the total weight of the composition. A particularly preferred use for the biocidal compounds of the present invention is in paint and paint bases.

The improved organic solubility and biocidal efficacy associated with the compounds of the present invention are expected to Provide advantages when used in a wide variety of paints, including indoor and outdoor household paints, industrial and commercial paints and in particular marine paints for use, for example, or ships hulls.

Typically, a paint composition will contain a resin, a pigment and various optional additives such as thickening agent(s), wetting agents and the like, as is well known in the art. The resin is preferably selected from the group consisting of vinyl, alkyl, epoxy, acrylic, polyurethane and polyester resins, and combinations thereof. The resin is preferably employed in an amount of between about 20% and about 80% based upon the weight of the paint or paint base.

In addition, the paint composition of the present invention contains optional additional additives which have a favorable influence on the viscosity, the wetting power and the dispersibility, as well as on the stability to freezing and electrolytes and on the foaming properties. If a marine paint is being fabricated, the paint preferably contains a swelling agent to cause the paint to gradually "slough off" in its marine environment, thereby causing renewed biocidal efficacy of newly exposed biocide at the surface of the paint in contact with the water medium of the marine environment. Illustrative swelling agents are naturally-occurring or synthetic clays, such as kaolin, montomorillonite (bentonite, clay mica (muscovite), and chlorite (hectonite), and the like. In addition to clays, other swelling agents, including natural or synthetic polymers, such as that commercially available as POLYMERGEL, have been found to be useful in the compositions of the present invention to provide the desired "sloughing off" effect. Swelling agents can be used singly or in combination. The total amount of optional additives is preferably no greater than 20% by weight, more preferably between about 1% and about 5% by weight, based upon the total weight of the paint composition.

Illustrative thickening agents include cellulose derivatives, for example methyl, hydroxyethyl, hydroxypropyl and carboxymethyl cellulose, poly(vinyl alcohol), poly (vinylpyrolidone), poly(ethylene-glycol), salts of poly(acrylic acid) and salts of acrylic acid/acrylamide copolymers.

Suitable wetting and dispersing agents include sodium polyphosphate, salts of low-molecular-weight poly(acrylic acid), salts of poly(ethane-sulfonic acid), salts of poly (vinyl-phosphonic acid), salts of poly(maleic acid) and salts of copolymers of maleic acid with ethylene, 1-olefins with 3 to 18 carbon atoms and/or styrene.

In order to increase the stability to freezing and electrolytes there may be added to the paint composition various monomer 1,2-diols, for example glycol, propylene-glycol-(1,2), and butylene-glycol-(1,2) or polymers thereof, or ethoxylated compounds, for example reaction Products of ethylene oxide with long-chain alkanols, amines, carboxylic acids, carboxylic acid amides, alkyd phenols, poly(propylene-glycol) or poly(butylene-glycol). The minimum temperature of film formation (white point) of the paint composition may be reduced by adding solvents, such as ethylene-glycol, butyl-glycol, ethyl-glycol acetate, ethyl-diglycol acetate, butyl-diglycol acetate, benzene or alkylated aromatic hydrocarbons. As defoaming agents there are suitable for example poly(propylene-glycol) and polysiloxanes.

The following examples are intended to illustrate, but in no way limit the scope of, the present invention. In the examples, all NMR chemical shifts are given in parts per million (ppm) using TMS as the reference (0 ppm). The term "g" denotes grams, "mol" denotes moles, "mmol" denotes millimoles and "Anal. Calcd" denotes analysis calculated.

Part A—Preparation of Compounds of this Invention

EXAMPLE I

Preparation of 3,5-Diphenyl-1-hydroxy-1,2-dihydroimidazole-2-thione

N-phenacylaniline was prepared according to the literature method of *J. Chem. Soc. Perkin Trans.* 1, pp. 1841 (1987) by J. L. Fourrey, J. Beauclaire and C. Wei Yuan. The material had a mp. of 97° C. after recrystallization from methylene chloride and ethanol. The NMR results were as follows: $^1$H NMR (200 MH$_2$, CDCl$_3$) 4.58 (2H, CH$_2$, S); 4.9 (1H, NH, S); 6.7 (3H, m); 7.2 (2H, t); 7.5 (3H, m); 8(2H, d); 13C NMR (CDCl$_3$) 50.3 (CH$_2$); 113 (CH); 117.8 (CH); 127.7 (CH); 128.9 (CH); 129.4 (CH); 133.8 (CH); 134.9 (Cq); 147.1 (Cq); 195 (C=O). O-Phenyl-N-(2-Oxo-2-phenylethyl) thiocarbamate was prepared as follows:

Phenyl chlorothionoformate (4 ml, 28.7 mmol) and K$_2$CO$_3$ (4 g, 28.7 mmol) were added to a solution of Phenacylaniline (5.5 g, 26 mmol) in dichloromethane (100 ml) (few drops of methanol were also added). The reaction mixture was stirred for 12 hr. at room temperature and the salt which precipitated was filtered. The solution was then washed successively with dilute sodium hydrogen carbonate, water and saturated aqueous sodium chloride and dried over MgSO$_4$. After filtration and evaporation of the solvent under vacuum, the resulting solid was crystallized from CH$_2$Cl$_2$/EtOH to give the thiocarbamate (8.09 g, 90%) as a yellow crystal. mp: 143° C. (CH$_2$Cl$_2$, EtOH; IR (CH$_2$Cl$_2$): 1702-1444-1220-1202-1180 cm$^{-1}$; $^1$H NMR (200 MHz, CDCl$_3$; 5.6 (2H, CH$_2$, s); 7 to 7.5 (13 H, m); 8 (2H, d); $^{13}$C NMR (CDCl$_3$): 62.4 (CH$_2$); 122.4 (CH); 122.6 (CH); 125.8 (CH); 126.5 (CH); 127.8 (CH); 128 (CH); 128.7 (CH); 129.1 (CH); 129.3 (CH); 133.6 (CH); 135.1 (Cq); 142.7 (Cq); 154.1 (Cq); 189.3 and 192 (C=O and C=S); Anal. Calcd for C$_{21}$H$_{17}$NO$_2$S; C,72.59; H, 4.93; N, 4.03; S, 9.23 Found: C, 72.68; H, 4.94; N, 4.04; S, 9.16.

The 3,5-diphenyl-1-hydroxy-1,2-dihydroimidazole-2-thione compound was prepared by dissolving 5 g (14.4 mmol) o-phenyl-N-(2-oxo-2-phenylethyl)-N-phenyl thiocarbamate in ethanol (30 ml) and to the solution were added Pyridine (5.8 ml, 72 mmol) and hydroxylamine hydrochloride (1.1 g, 15.84 mmol). The reaction mixture was refluxed for 8 hr and the solvent was then evaporated. The crude was dissolved in dichloromethane and washed with water and brine. After drying over MgSO$_4$, filtration and evaporation of the solvent under vacuum, recrystallization from EtOH gave the desired 3,5-diphenyl-1-hydroxy-1,2-dihydroimidazole-2-thione mp: 163° C. dec (EtOH); IR (CH$_2$Cl$_2$) 2971-1545-1497-1382-1362-1132-1111 cm$^{-1}$, $^1$H NMR (200 MHz, CDCl$_3$: DMSO 1:1): 7 (1H, CH=,s); 7.4 (6H, m); 7.7 (4H, m); 11.4 (1H, OH, br); $^{13}$C NMR (CDCl$_3$:DMSO 1:1): 110.6 (CH=); 125.1 (CH); 126.1 (CH); 126.5 (CH); 127.7 (CH); 128 (CH); 128.1 (CH); 128.5 (CH); 137.4 (Cq); 158.2 (Cq). Calcd for : C$_{15}$H$_{12}$N$_2$OS: C, 67.13; H, 4.51; N, 10.44; S, 11.95. Found: C, 67.10; H, 4.53; N, 10.41; S, 11.87.

EXAMPLE II 3-(p-Methopyphenyl phenyl-1-hydroxy-1,2-dihydroimidazole-2-thione

N-phenyl-p-anisidine was prepared according to the literature method of J. L. Fourrey, J. Beauclaire and C. Wei Yuan in *J. Chem. Soc. Perkin Trans* 1, pp. 1841 (1987). The material had a mp. of 89°-90° C. after recrystallization from methylene chloride and hexane. The NMR and IR results were as follows: IR (CH$_2$Cl$_2$): 3397-1689-1510-1216 cm$^{-1}$; $^1$H NMR (200 MHz, CDCl$_3$): 3.75 (3H, CH$_3$O, s); 4.4 (1H, NH, br); 4.55 (2H, CH$_2$, s); 6.65 (2H, d); 6.8 (2H, d); 7.4 to 7.6 (3H, m); 8 (2H, d); $^{13}$C NMR (CDCl$_3$): 51.2 (CH$_2$); 55.7 (OCH$_3$); 114.2 (CH); 115 (CH); 127.7 (CH); 127.8 (CH); 128.8 (CH); 133.7 (CH); 135 (Cq); 141.4 (Cq); 152.2 (Cq); 195.4 (C=O); O-phenyl-N-(2-oxo-2-phenylethyl)-N-p-methoxyphenyl thiocarbamate was prepared as follows: Phenyl chlorothionoformate (240 microliters, 1.73 mmol) and K (240 mg, 1.73 mmol) were added to a solution of N-Phenyl-p-anisidine (400 mg, 1.66 mmol) in dichloromethane (10 ml) (few drops of methanol also added). The reaction mixture was stirred for 7 hr. at room temperature and the salt which precipitated was filtered. The solution was then washed successively with dilute sodium hydogen carbonate, water and saturated aqueous sodium chloride. After drying over MgSO$_4$, filtration and evaporation, the crude material was chromatographied on silica gel (eluent ether/hexane 1:1) to give O-phenyl-N-(2-oxo-2-phenyl ethyl)-N-P-methoxy phenyl thiocarbamate as a yellow solid mp. 50° C. The IR, NMR and C,H,N analyses were as follows: IR (CH$_2$Cl$_2$): 1700-1592-1508-1445-1221-1203 1181 cm$^{-1}$; $^1$H NMR (200 MHz, CDCl$_3$); 3.78 (3H, CH$_3$O, s); 5.6 (2H, CH$_2$, s); 6.9 (2H, m); 7.1 to 7.6 (10 H, m); 7.95 (2H, d); $^{13}$C NMR (CDCl$_3$): 55.4 (CH$_3$O); 62.6 (CH$_2$); 114.4 to 129 (CH); 133.6 (Cq); 135.1 (Cq); 135.4 (Cq); 154 (Cq); 159 (C—OCH$_3$); 189.7 and 192.2 (C=O and C=S); Anal. Calcd for $C_{22}H_{19}NO_3S$: C,70.00; H, 5.07; N, 3.71; S, 8.49 Found: C, 70.08; H, 5.11; N, 3.74; S, 8.42.

The thiohydroxamine acid, 3-(p-methoxyphenyl)-5-phenyl-1-hydroxy-1,2-dihydroimidazole-2-thione, was prepared from the thiocarbamate in a manner similar to that used in Example I. The 3-(p-methoxyphenyl)-5-phenyl-1-hydroxy-1,2-dihydroimidazole-2-thione was recrystallized from methylene chloride/hexane to give white crystalline material. mp: 168° C. (dec); IR ($CH_2Cl_2$): 2800-1756-1510-1383-1361-1241-1133 $cm^{-1}$; $^1H$ NMR (200 MHz, $CDCl_3$: DMSO 1:1): 3.82 (3H, $OCH_3$, s); 6.5 (2H, d); 7.15 (1H, CH=, s); 7.4 (3H, m); 7.54 (2H, d); 7.71 (2H, d); 11.85 (1H, OH, br); $^{13}C$ NMR ($CDCl_3$: DMSO 1:1): 54 ($OCH_3$): 110.6 (CH=); 112.6 (CH); 125.6 (CH); 125.7 (CH); 127 (CH); 127.2 (CH); 129.5 (Cq); 157.6 (CH); Anal. Calcd for $C_{16}H_{14}N_2O_2S$: C, 64.40; H, 4.73; N, 9.39; S,10.74 Found C, 64.48; H, 4.24; N,9.43; S, 10.68.

EXAMPLE III

Preparation of 5-(p-Methoxyphenyl)-3-phenyl-1-hydroxy-1,2-dihydroimidazole-2-thione N-p-Methoxyphenacylaniline was prepared according to the literature method of J. L. Fourrey, J. Beauclaire and C. Wei Yuan in *J. Chem. Soc. Perkin Trans* 1 pp. 1841 (1987). The material had a mp of 105°-106° C. after recrystallization from methylene chloride and hexane. The analytical results were as follows: IR ($CH_2Cl_2$) 3400-1679-1600-1503-1350-1223-1172 $cm^{-1}$; $^1H$ NMR (200 MHz, $CDCl_3$) 3.88 (3H, $CH_3O$, s); 4.53 (1H, $CH_2$, s); 4.63 (1H, NH, br); 6.71 (3H, m); 6.95 (2H, d); 7.21 (2H, m); 7.98 (2H, d); $^{13}C$ NMR ($CDCl_3$: 49.8 ($CH_2$); 55.5 ($OCH_3$); 113 (CH); 117.6 (CH); 127.8 (Cq); 129.3 (CH); 130 (CH); 147.1 (Cq); 164 (C—$OCH_3$); 193.4 (C=O); N-(2-oxo-2-p-methoxyphenyl)S-N-phenyl-S-phenyl dithiocarbamate was prepared as follows: Phenyl chlorodithioformate (1.64 ml, 11.55 mmol) and $K_2CO_3$ (1.6 g, 11.55 mmol) were added to a solution of N-p-methoxyphenylacylaniline (2.53 g, 10.5 mmol) in 20 ml of dichloromethane (a few drops of methanol were also added). The reaction mixture was stirred for 12 hr. at room temperature. The solution was diluted with dichloromethane and then washed successively with water and saturated aqueous sodium chloride. After drying over $MgSO_4$, filtration and evaporation of the solvent under vacuum, crystallization from dichloromethane/hexane gave the dithiocarbamate, N-(2-oxo-2-p-methoxyphenyl)-N-phenyl-S-phenyldithiocarbamate with mp. 175° C. (decomposed) and the following analytical data: IR ($CH_2Cl_2$):

1687-1598-1368-1218-1169-1112 $cm^{-1}$; $^1H$ NMR (200 MHz, $CDCl_3$) 3.83 (3H, $CH_3O$, s); 5.68 (2H, $CH_2$, s); 6.9 (2H, d); 7.43 (8H, m); 7.65 (2H, m); 7.94 (2H, d); $^{13}C$ NMR ($CDCl_3$: 55.4 ($CH_3O$); 63.3 ($CH_2$); 113.8 (CH); 128 (CH); 128.9 (CH); 129.4 (CH); 129.6 (CH); 129.8 (CH); 130.2 (CH); 132.5 (Cq); 136.6 (CH); 144.2 (Cq); 163.7 (Cq); 190 (C=O); 201.1 (C=S).

The dithiocarbamate (2 g, 5.089 mmol) was dissolved in 20 ml of ethanol and 5 ml of THF. To the solution was added pyridine (2 ml, 25 mmol) and hydroxylamine hydrochloride (424 mg, 6.1 mmol). The reaction mixture was refluxed for 20 hr. and the solvent was then evaporated. The crude was taken up in ether and the solid filtrated. The product was redissolved in dichloromethane and washed with water. After drying over $MgSO_4$, filtration and evaporation of the solvent under vacuum, recrystallization from $CH_2Cl_2$/hexane gave 5-(p-methoxyphenyl)-3-phenyl-1-hydroxy-1,2-dihydroimidazol-2-thione, mp 176° C. (decomposed) as a white solid. $^1H$ NMR (200 MHz, $CDCl_3$:DMSO 1:1): 3.83 (3H, $OCH_3$, s); 6.98 (3H, CH=and Harom, m); 7.5 (3H, m); 7.66 (4H, m); 11.59 (1H, OH, s); $^{13}C$ NMR ($CDCl_3$ DMSO 1:1): 54.9 ($OCH_3$); 110.1 (CH=); 113.7 (CH); 118.7 (Cq); 125.3 (CH); 127.6 (CH); 128.2 (CH); 128.5 (CH); 137.7 (Cq); 159.3 (Cq); Anal. Calcd for $C_{16}H_{14}N_2O_2S$: C, 64.40; H, 4.73; N, 9.39; S, 10.74 Found: C, 64.14; H, 4.77; N, 9.27; S, 10.62.

Part B - Antimicrobial Testing of the Above Compounds

Determination of the Minimum Inhibitory Concentrations (MIC's) for the Compounds Prepared in Part A Solutions of the experimental compounds in dimethyl sulfoxide and an aqueous solution of sodium pyrithione were serially diluted in nutrient broth (Tryptic Soy Broth for bacteria and Sabouraud Dextrose Broth for fungi) in microtiter plates. Equal volumes of a broth supension of bacteria ($10^6$ CFU/ml) or fungi ($10^5$ cells or spores/ml) were added to each dilution, and the plates were incubated at 37° C. (bacteria and yeast) or 28° C. (molds). Bacteria, yeast and molds were incubated two, five and seven days respectively before determining the highest inhibitory dilution.

TABLE I

| Compounds | MIC (ppm) | | | | | |
|---|---|---|---|---|---|---|
| | A | B | C | D | E | F |
| 1 | 64 | 256 | 2 | 2 | 8 | 16 |
| 2 | 32 | 2048 | 4 | 8 | 64 | 1024 |
| 3 | 32 | 32 | 2 | 16 | 512 | 512 |
| Pyrithione, sodium salt | 8–32 | 4–8 | 4–16 | 2–32 | 32–128 | 64–128 |

A = *E. Coli*, B = *S. aureus*, C = *Candida albicans*, D = *Aureobasidium pullulans*, E = *Aspergillins niger*, F = *Fusarium*

It is apparent from Table I that for the tested organisms the compounds of the present invention in some instances have better antimicrobial activity than sodium pyrithione. Consequently, the compounds of the present invention in addition to having a solubility advantage in organic solvents also in certain instances have increased antimicrobial activity. This leads to a third aspect of this invention which relates to a process for inhibiting the growth of microorganisms by contacting said microorganisms which an antimicrobial effective amount of the compound of this invention.

What is claimed is:

1. A composition comprising a compound selected from the group consisting of 3,5-diphenyl- and substituted 3,5-diphenyl-1-hydroxy-1,2-dihydroimidazole-2-thiones, and combinations thereof.

2. The composition of claim 1 wherein said substituted phenyl comprises a substituent selected from the group consisting of halogen, lower alkyl containing between one and six carbons, lower alkoxy containing between one and six carbons, carboxylic acid, carboxylic acid ester(s), and nitro groups.

3. A process for producing antimicrobial compounds which comprises the following steps:
    (a) reacting aniline or substituted aniline(s) with phenacyl halide or substituted phenacyl halide(s) in the presence of a base in an organic solvent to form N-phenacylaniline or substituted N-phenacylaniline(s);

(b) reacting N-phenylacylaniline or substituted N-phenylacylaniline(s) with chlorothiono (or dithio) formic acid esters and a base in an organic solvent to form N-(2-oxo-2-phenylethyl)-N-phenylthiono (or dithio) carbamic acid ester(s) or substituted N-(2-oxo-2-phenylethyl)-N-phenylthiono (or dithio) carbamic acid ester(s), and (c) reacting N-(2-oxo-2-phenylethyl)-N-phenylthiono (or dithio) carbamic acid esters or substituted N-(2-oxo-2-phenylethyl)-N-phenylthiono (or dithio) carbamic acid esters with hydroxylamine hydrochloride and a base in an organic solvent to form 3,5-diphenyl-1-hydroxy-1,2-dihydroimidazole-2-thione or substituted 3,5-diphenyl-1-hydroxy-1,2-dihydroimidazole-2-thione.

4. The process of claim 3 wherein said base employed steps (a), (b) and (c) thereof is selected from the group consisting of pyridine, triethylamine and other tertiary amine bases, potassium carbonate, aniline or substituted anilines, 1,4-diazabicyclo(2.2.2)octane, 1,8-diazabicyclo(5.4.0)undec-7-ene, 1,5-diazabicyclo(4.3.0)non-5-ene, t-butyltetramethyl-guanidine, and combinations thereof.

5. The process of claim 3 wherein said organic solvent is selected from the group consisting of alcohol, ether, and acetone, methylene chloride, benzene, toluene, pyridine, tetrahydrofuran, and combinations thereof.

6. A composition comprising an antimicrobial effective amount of a compound selected from the group consisting of 3,5-diphenyl- and substituted 3,5-diphenyl-1-hydroxy-1,2-dihydroimidazole-2-thiones, and combinations thereof, and at least one component selected from the group consisting of soaps, shampoos, skin care medicaments, cosmetics and paints.

7. The composition of claim 6 wherein said compound is present in said composition in an amount of between about 0.01 and about 10 weight percent based upon the total weight of the composition.

8. The composition of claim 6 wherein said composition comprises said compound and a paint and wherein said paint comprises a resin selected from the group consisting of vinyl, alkyl, epoxy, acrylic, polyurethane and polyester resins, and combinations thereof.

9. The composition of claim 8 wherein said resin is employed in said composition in an amount of between about 20% and about 80% based upon the weight of the composition.

10. A method of inhibiting the growth of microorganisms by contacting said microorganisms with an antimicrobial effective amount of a compound selected from the group consisting of 3,5-diphenyl- and substituted 3,5-diphenyl-1-hydroxy-1,2-dihydroimidazole-2-thiones, and combinations thereof.

11. The method of claim 10 wherein said substituted phenyl comprises a substituent selected from the group consisting of halogen, lower alkyl containing between one and six carbons, lower alkoxy containing between one and six carbons, carboxylic acid, carboxylic acid ester(s), and nitro groups.

* * * * *